(12) United States Patent
Seales

(10) Patent No.: US 11,191,660 B2
(45) Date of Patent: Dec. 7, 2021

(54) METHOD OF REHABILITATING AN INJURED LEG OF A QUADRUPED

(71) Applicant: Rebecca Seales, Port Isabel, TX (US)

(72) Inventor: Rebecca Seales, Port Isabel, TX (US)

(*) Notice: Subject to any disclaimer, the term of this patent is extended or adjusted under 35 U.S.C. 154(b) by 718 days.

(21) Appl. No.: 16/106,226

(22) Filed: Aug. 21, 2018

(65) Prior Publication Data
US 2020/0060861 A1 Feb. 27, 2020

(51) Int. Cl.
| | |
|---|---|
| *A61F 5/04* | (2006.01) |
| *A01K 15/04* | (2006.01) |
| *A61F 5/37* | (2006.01) |
| *A61D 99/00* | (2006.01) |
| *A01K 29/00* | (2006.01) |

(52) U.S. Cl.
CPC .............. *A61F 5/04* (2013.01); *A01K 15/04* (2013.01); *A61D 99/00* (2013.01); *A61F 5/3738* (2013.01); *A01K 29/00* (2013.01)

(58) Field of Classification Search
CPC ...... A01K 15/04; A01K 15/02; A01K 27/002; A01K 27/003; A01K 29/00; A61D 99/00; A61D 9/00; A61F 5/04; A61F 5/3738
USPC ....... 119/818, 816, 702, 792, 907, 817, 856, 119/819; 54/71, 72; 482/124
See application file for complete search history.

(56) References Cited

U.S. PATENT DOCUMENTS

| | | | | |
|---|---|---|---|---|
| 597,317 | A * | 1/1898 | Ellsworth | A01K 15/04 119/818 |
| 2,534,727 | A * | 12/1950 | Moyle | A01K 15/04 54/71 |
| 2,650,590 | A * | 9/1953 | Moore | A47D 13/086 128/882 |
| 4,528,944 | A * | 7/1985 | Reed | A01K 15/04 119/702 |
| RE32,547 | E * | 11/1987 | Reed | A01K 15/02 119/702 |
| 5,165,696 | A | 11/1992 | Saha | |
| 5,348,292 | A | 9/1994 | Norman, Sr. | |
| 5,472,000 | A | 12/1995 | Olsen | |
| 5,718,672 | A | 2/1998 | Woodman | |
| 6,354,247 | B1 * | 3/2002 | Andrews | A01K 15/02 119/818 |
| 6,585,672 | B1 * | 7/2003 | Crompton | A61F 5/0193 128/869 |
| 7,107,940 | B2 | 9/2006 | Abinanti | |
| 7,150,248 | B2 * | 12/2006 | Hodl | A01K 15/02 119/818 |
| 8,171,892 | B1 * | 5/2012 | Horgan | A01K 27/002 119/792 |

(Continued)

OTHER PUBLICATIONS

USPTO Office Action for U.S. Appl. No. 11/333,525 dated Oct. 17, 2007.

(Continued)

*Primary Examiner* — Yvonne R Abbott-Lewis
(74) *Attorney, Agent, or Firm* — Coats & Bennett, PLLC

(57) ABSTRACT

A method of rehabilitating an injured leg of a quadruped. The method can include attaching a strap to the foreleg and hindleg on the same side of the quadruped. The strap causes the un-injured leg to applying a moving force to the injured leg. This force moves the injured leg and requires the quadruped to more fully use the injured leg leading to rehabilitation.

13 Claims, 6 Drawing Sheets

(56) References Cited

U.S. PATENT DOCUMENTS

| | | | |
|---|---|---|---|
| 8,459,212 B2* | 6/2013 | Meisenbach | A01K 27/005 |
| | | | 119/856 |
| 9,497,933 B2* | 11/2016 | Eldevik | A01K 29/00 |
| 2005/0103283 A1* | 5/2005 | Penzak | A01K 15/04 |
| | | | 119/816 |
| 2020/0060861 A1* | 2/2020 | Seales | A01K 15/04 |
| 2020/0205377 A1* | 7/2020 | Kamath | A01K 27/003 |
| 2021/0121278 A1* | 4/2021 | Pierce | A61D 9/00 |

OTHER PUBLICATIONS

USPTO Office Action for U.S. Appl. No. 11/333,525 dated Apr. 3, 2008.
USPTO Office Action for U.S. Appl. No. 11/333,525 dated Nov. 14, 2008.
Amendment and Response to USPTO Office Action for U.S. Appl. No. 11/333,525 dated Oct. 17, 2007 filed Jan. 10, 2008.
Amendment and Response to USPTO Office Action for U.S. Appl. No. 11/333,525 dated Apr. 3, 2008 filed Jul. 3, 2008.
Appeal Brief for U.S. Appl. No. 11/333,525, filed Sep. 10, 2008.

* cited by examiner

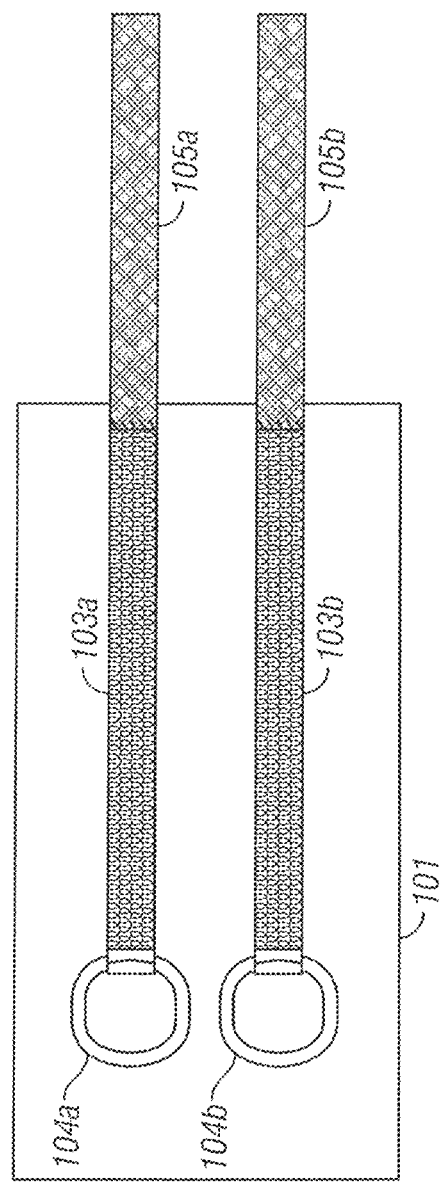

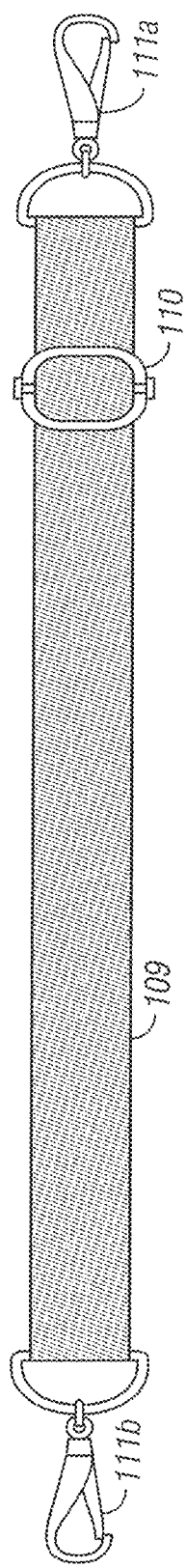

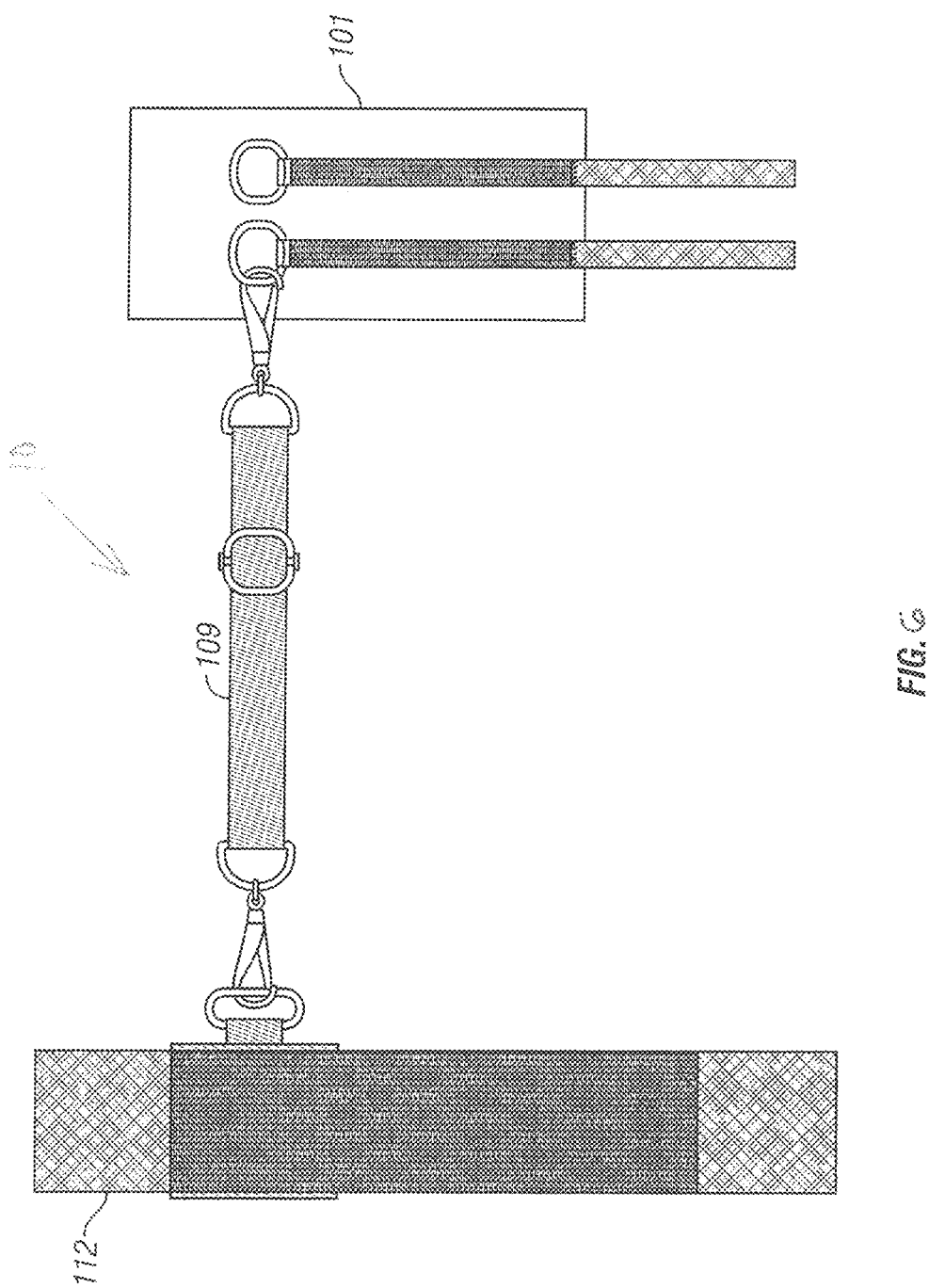

METHOD OF REHABILITATING AN INJURED LEG OF A QUADRUPED

BACKGROUND

Quadrupeds are animals that walk and run using four legs. Examples of quadrupeds include but are not limited to dogs, cats, and horses. Quadrupeds often have difficulty with rehabilitating an injured leg. The quadruped tends to protect the leg after injury and not use it during movement such as walking or running. As a result, the injured leg may take an extended time to heal. Further, the injured leg may atrophy and the quadruped may never again gain full use of the leg.

Devices are available to individually protect the injured leg. These can include various bandages and casts that are attached to the injured leg. However, these devices do not rehabilitate the injured leg when worn by the quadruped.

SUMMARY

One aspect is directed to a method of rehabilitating an injured leg of a quadruped. The method includes attaching a strap to an injured leg of a quadruped and to a non-injured leg of the quadruped with each of the injured leg and the non-injured leg being on a same side of the quadruped. The method also includes monitoring movement of the quadruped with the non-injured leg applying a force to the injured leg during a portion of the movement and with the injured leg moving forward and backward during the movement.

In another aspect, the method also includes maintaining a foreleg and a hindleg of an opposing side of the quadruped unencumbered to support the quadruped during the movement.

In another aspect, the method also includes attached the strap between a knee and a foot to both the injured leg and the non-injured leg.

In another aspect, monitoring the movement of the quadruped includes viewing the quadruped during the movement.

In another aspect, the method also includes removing the strap from the injured leg and the non-injured leg after the movement.

In another aspect, the method also includes monitoring the strap to become slack during the movement of the quadruped.

In another aspect, the method also includes monitoring the injured leg that is the hindleg of the quadruped and with the strap being in tension and pulling the hindleg forward during a first portion of the stride and for the strap to be slack without applying a force to the hindleg during a second portion of the stride.

In another aspect, the method also includes attaching a first end of the strap to the injured leg and a second end of the strap to the non-injured leg.

One aspect is directed to a method of rehabilitating an injured leg of a quadruped. The method includes attaching a strap to an injured leg of a quadruped and to a non-injured leg of the quadruped with each of the injured leg and the non-injured leg being on a same side of the quadruped. The method includes monitoring the strap during strides of the quadruped with the strap configured to be in tension during a first portion of the strides of the quadruped and to be slack during a second portion of the strides.

In another aspect, the method also includes attaching the strap to the injured leg that is a hindleg of the quadruped and to the non-injured leg that is a foreleg of the quadruped, and monitoring the strap during the strides to be in tension during a forward step of the foreleg and to be slack during a return step of the foreleg.

In another aspect, the method also includes maintaining a foreleg and a hindleg of an opposing side of the quadruped unencumbered to support the quadruped during the strides.

In another aspect, the method also includes attached the strap between a knee and a foot of both the injured leg and the non-injured leg.

In another aspect, the method also includes removing the strap from the injured leg and the non-injured leg after the strides.

One aspect is directed to a method of rehabilitating an injured leg of a quadruped. The method includes attaching a first end of a strap to an injured leg of a quadruped. The method includes attaching a second end of the strap to a non-injured leg of the quadruped with the strap in tension during a first portion of each of the strides to force the injured leg to move with the non-injured leg and the strap being slack during a second portion of each of the strides.

In another aspect, the method also includes attaching the strap to the injured leg and the non-injured leg on a same side of the quadruped.

In another aspect, the method also includes leaving the legs on the opposing side of the quadruped unencumbered to support the quadruped during the strides.

The various aspects of the various embodiments may be used alone or in any combination, as is desired.

BRIEF DESCRIPTION OF THE DRAWINGS

FIG. 4 is a plan view of a first attachment of a strap.

FIG. 5 is a plan view of an intermediate member of a strap.

FIG. 6 is a plan view of a strap.

DETAILED DESCRIPTION

The present application is directed to a method of rehabilitating an injured leg of a quadruped. The method includes attaching a strap to the foreleg and hindleg on the same side of the quadruped. The strap causes the non-injured leg to apply a moving force to the injured leg. This force moves the injured leg and requires the quadruped to more fully use the injured leg. This use and movement leads to faster and more complete rehabilitation of the injured leg.

Figure 1A:
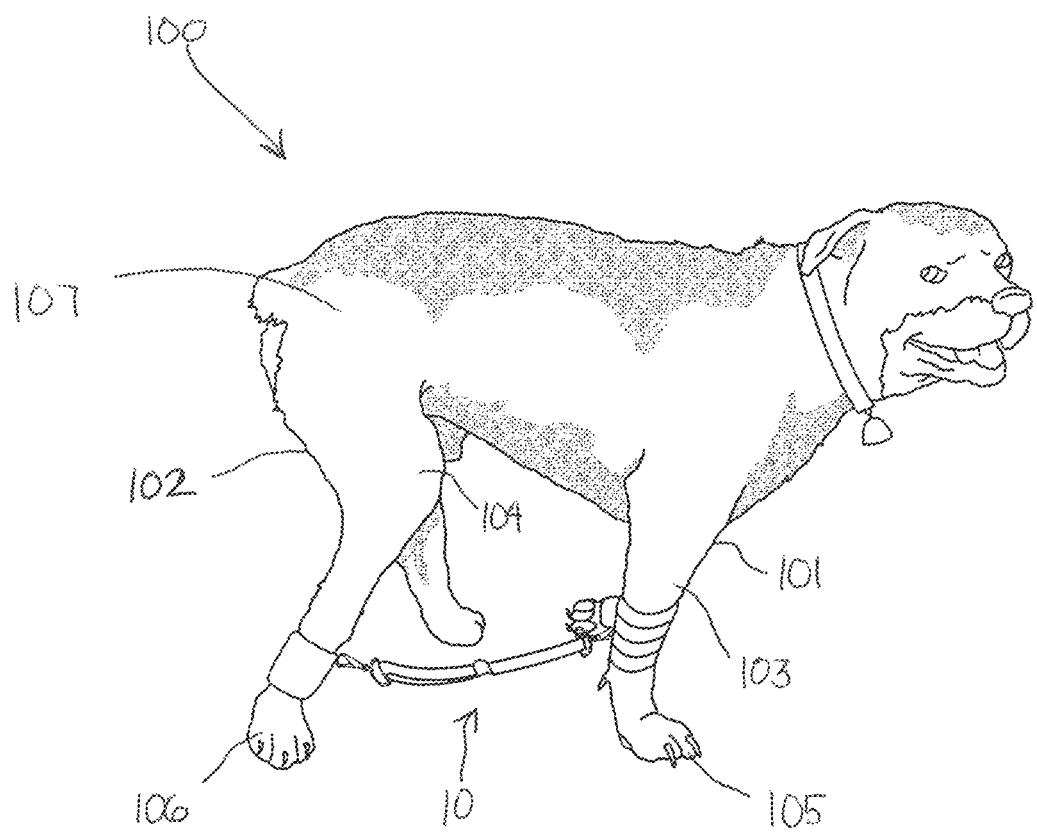
FIG. 1A is a perspective view of a strap attached to a quadruped.
Figure 1B:
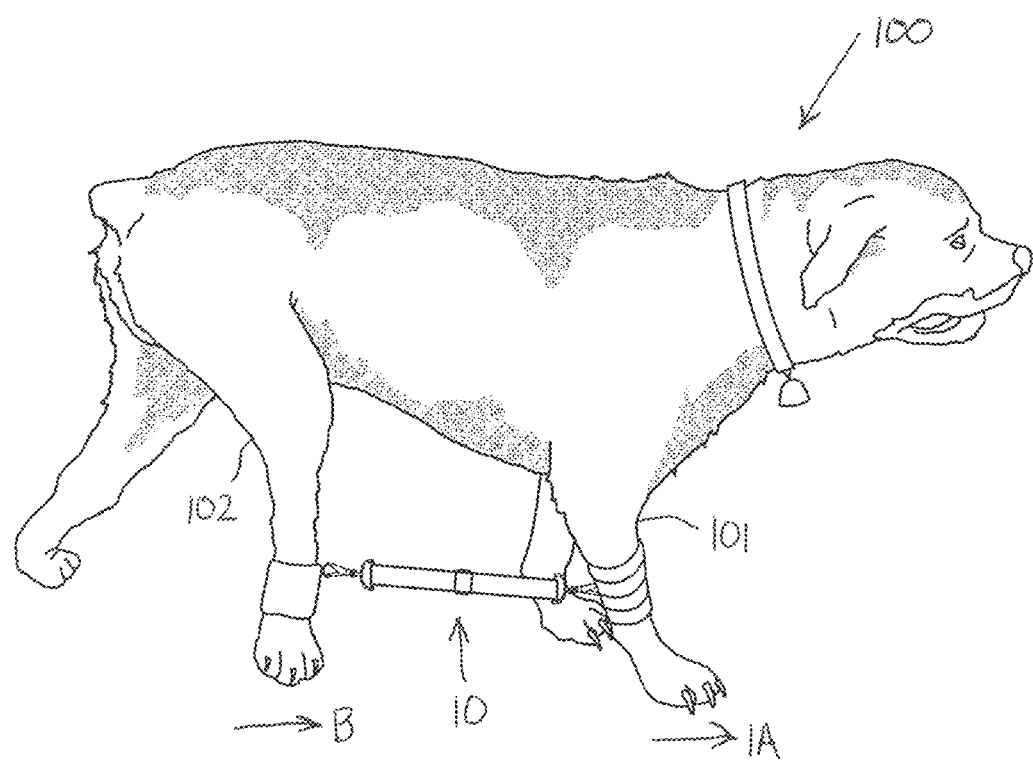
FIG. 1B is a perspective view of the quadruped of FIG. 1A moving the injured leg using the strap.

FIGS. 1A and 1B illustrate a method of rehabilitating a quadruped 100. FIGS. 1A and 1B specifically illustrate the quadruped 100 being a dog, although the method is also applicable to other quadrupeds 100. In this example, the hindleg 102 of the quadruped 100 is the injured leg. The strap 10 is connected to the non-injured foreleg 101 and the injured hindleg 102 on a same side of the quadruped 100. In this example, the strap 10 is connected on the right side of the quadruped 100. The legs on the opposing side (in this example, the left side) are non-encumbered to allow these legs to support the quadruped 100 during the movement.

The strap 10 can be connected when the quadruped 100 is either sitting or standing. Further, the strap 10 can be connected to the foreleg 101 and the hindleg 102 at points away from the main body 107. This positioning has been determined to cause the quadruped 100 to move the injured leg a greater amount than if the strap 10 were connected at a point closer to the main body 107. This positioning can include attaching the strap 10 between the knee 103 and foot 105 of the foreleg 101 and the knee 104 and foot 106 of the hindleg 102. Other methods can include attaching the strap to one or both of the foreleg 101 and hindleg 102 closer to the main body 107.

When taking strides during walking and running, the quadruped 100 moves the non-injured leg (e.g., the foreleg 101 in FIGS. 1A and 1B) forward in the direction of arrow A as illustrated in FIG. 1B. This first portion of the stride causes the strap 10 to pull the hindleg 102 forward in the direction of arrow B. This motion uses the muscles in the hindleg 102 thus facilitating rehabilitation of the hindleg 102.

During the second portion of the stride, the quadruped 100 is forced to use the injured hindleg 102 to complete the stride. This movement further facilitates rehabilitation of the injured leg. The movement of the injured leg during the first and second portions of the stride provide for motion and muscle use within the injured leg to facilitate the rehabilitation.

The strap 10 is constructed to apply force to the injured leg during one portion of the stride, and to not inhibit movement of the injured leg during the second portion of the stride. With an injured hindleg 102 as an example, the strap 10 pulls the injured leg during the first portion of the stride (i.e., the foreleg 101 moving forward relative to the main body 107). The strap 10 is slack during the second portion of the stride (i.e, the foreleg 101 moving backward relative to the main body 107). In some embodiments, the strap 10 can remain in tension during the second portion of the stride when the quadruped 100 maintains the foreleg 101 and hindleg 102 separated apart.

Figure 2:
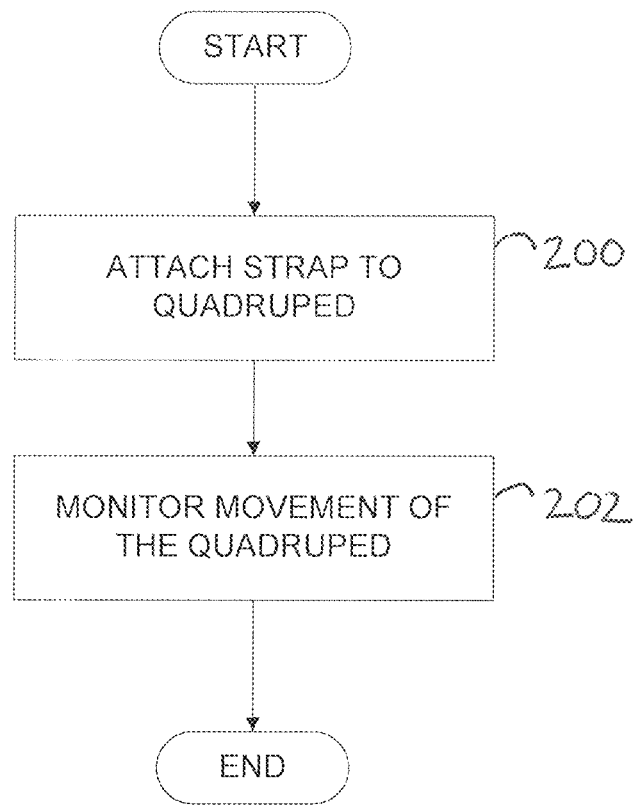
FIG. 2 is a flowchart diagram of a method of using a strap to rehabilitate an injured leg of a quadruped.

FIG. 2 illustrates a method of using the strap 10 to rehabilitate an injured leg of a quadruped. The strap 10 is attached to the quadruped (block 200). This includes attaching the strap 10 to the injured leg and to the non-injured leg that is on the same side of the quadruped. The legs on the other side of the quadruped are left unencumbered so they can provide support to the quadruped during the movement.

Prior to or after the strap 10 is attached to the quadruped 100, the strap 10 can be adjusted. This can include adjusting the length to be about equal to a normal stride length of the quadruped 100. This length provides for a full range of movement of the injured leg when the non-injured leg provides the movement force. This also allows for the quadruped 100 to have a normal stride length. This may also provide for the quadruped 100 to better accept the strap 10 and not attempt to remove the strap 10.

Once the strap 10 is attached, the user monitors the movement of the quadruped (block 202). This can include visually observing the quadruped 100 during the strides to ensure the strap 10 is providing the necessary force to move the injured leg. This can also include visually observing the quadruped 100 to ensure the injured leg is moving during the non-assisted portion of the stride. If necessary, the length and/or positioning of the strap 10 can be adjusted.

The strap 10 can remain on the quadruped 100 for an extended period of time. For example, the strap 10 can remain on the animal for a day, multiple days, weeks, etc. Alternatively, the strap 10 can be removed after a predetermined period of time. Further, the strap 10 can be used as part of a regiment in which the times are extended as the injured leg is rehabilitating. For example, the strap 10 can remain on the quadruped 100 for a first time period during the first day (e.g., 1 hour). The strap 10 can then remain on for a longer period of time during the next day (e.g., 2 hours). The time can be extended as necessary depending upon the quadruped 100. Further, the monitoring can determine when rehabilitation is at a point in which the strap 10 is no longer necessary.

Figure 3:
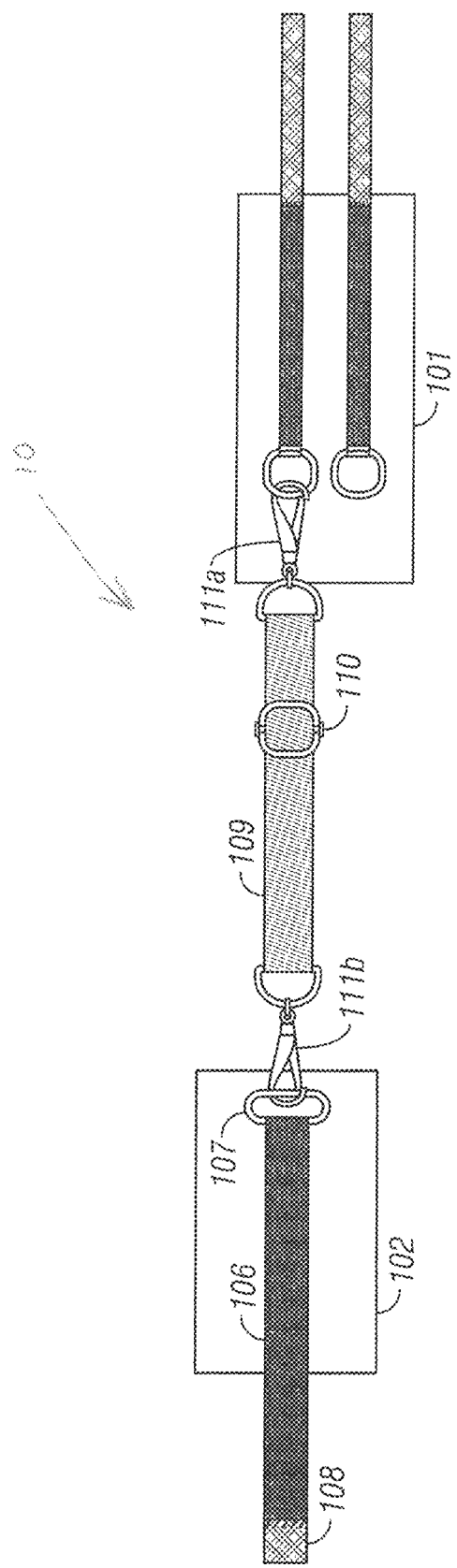
FIG. 3 is a plan view of a strap.

FIG. 3 illustrates a strap 10 configured to be attached to the foreleg 101 and hindleg 102 of a quadruped 100. The strap 10 generally includes first and second attachments 101, 102 and an intermediate section 109. The first and second attachments 101, 102 can be made from various materials, including a medical cloth. This can include a thin layer of soft non-matting material that extends around a foam pad. The thickness of the first and second attachments 101, 102 can range from approximately 3/16" for a small quadruped 100 to ½" or more for a larger quadruped 100.

FIG. 4 illustrates the first attachment 101. One example includes the first attachment 101 being approximately 6" long (six inches) and 3" (three inches) in width. A pair of straps 103(*a*), 103(*b*) is sewn to the cloth. Metal rings 104*a*, 104*b* are positioned approximately two inches back from the end of the material. Straps 105*a*, 105*b* of approximately four inches of hook-and-loop material are sewn to the ends of the straps 103*a*, 103*b* and extend past the material making the overall length of the first attachment 101 to be about 10".

The second attachment 102 is formed of medical cloth approximately 2⅓" (two and one-third inches) in width and 5" (five inches) in length. The second attachment 102 includes a 2½" wide hook-and-loop strap 106 sewn from a middle of the material with a ring or loop 107 attached at the middle of the material. One end of the hook-and-loop strap 106 is sewn to a strap 108 that is about 2" (two inches) of hook-and-loop material, making the total length of the second attachment 102 about 13" (thirteen inches) overall.

The intermediate section 109 extends between the first and second attachments 101, 102. As illustrated in FIGS. 3 and 5, the intermediate section 109 can include a strap constructed from a high weave material. An adjustment buckle 110 can be positioned along the strap to adjust the length. Hooks 111*a*, 111*b* can be attached to the ends to couple together the first and second attachments 101, 102. The intermediate strap 109 can be about 1" (one inch) wide.

FIG. 6 illustrates another strap 10 that includes an intermediate member 109 attached to a first attachment 101 and a second attachment 112. The first and second attachments 101, 112 can be aligned at various orientations.

FIGS. 3-6 illustrate examples of straps 10. The straps 10 can include various configurations. Further, the straps 10 can be constructed to be flexible in length or can be constructed to have a rigid length.

Spatially relative terms such as "under", "below", "lower", "over", "upper", and the like, are used for ease of description to explain the positioning of one element relative to a second element. These terms are intended to encompass different orientations of the device in addition to different orientations than those depicted in the figures. Further, terms such as "first", "second", and the like, are also used to describe various elements, regions, sections, etc and are also not intended to be limiting. Like terms refer to like elements throughout the description.

As used herein, the terms "having", "containing", "including", "comprising" and the like are open ended terms that indicate the presence of stated elements or features, but do not preclude additional elements or features. The articles "a", "an" and "the" are intended to include the plural as well as the singular, unless the context clearly indicates otherwise.

The present invention may be carried out in other specific ways than those herein set forth without departing from the scope and essential characteristics of the invention. The present embodiments are, therefore, to be considered in all respects as illustrative and not restrictive, and all changes coming within the meaning and equivalency range of the appended claims are intended to be embraced therein.

What is claimed is:

1. A method of rehabilitating an injured leg of a quadruped, the method comprising:
    attaching a strap to an injured leg of a quadruped and to a non-injured leg of the quadruped, each of the injured leg and the non-injured leg being on a same side of the quadruped;
    monitoring movement of the quadruped with the non-injured leg applying a force to the injured leg during a portion of the movement and with the injured leg moving forward and backward during the movement; and
    maintaining a foreleg and a hindleg of an opposing side of the quadruped unencumbered to support the quadruped during the movement.

2. The method of claim 1, further comprising attaching the strap between a knee and a foot to both the injured leg and the non-injured leg.

3. The method of claim 1, wherein monitoring the movement of the quadruped comprises viewing the quadruped during the movement.

4. The method of claim 1, further comprising removing the strap from the injured leg and the non-injured leg after the movement.

5. The method of claim 1, further comprising monitoring the strap to become slack during the movement of the quadruped.

6. The method of claim 1, further comprising monitoring the injured leg that is the hindleg of the quadruped and with the strap being in tension and pulling the hindleg forward during a first portion of the stride and for the strap to be slack without applying a force to the hindleg during a second portion of the stride.

7. The method of claim 1, further comprising attaching a first end of the strap to the injured leg and a second end of the strap to the non-injured leg.

8. A method of rehabilitating an injured leg of a quadruped, the method comprising:
    attaching a strap to an injured leg of a quadruped and to a non-injured leg of the quadruped, each of the injured leg and the non-injured leg being on a same side of the quadruped;
    monitoring the strap during strides of the quadruped; and
    maintaining a foreleg and a hindleg of an opposing side of the quadruped unencumbered to support the quadruped during the strides;
    the strap configured to be in tension during a first portion of the strides of the quadruped and to be slack during a second portion of the strides.

9. The method of claim 8, further comprising attaching the strap to the injured leg that is a hindleg of the quadruped and to the non-injured leg that is a foreleg of the quadruped and with the strap in tension during a forward step of the foreleg and to be slack during a return step of the foreleg.

10. The method of claim 8, further comprising attached the strap between a knee and a foot of both the injured leg and the non-injured leg.

11. The method of claim 8, further comprising removing the strap from the injured leg and the non-injured leg after the strides.

12. A method of rehabilitating an injured leg of a quadruped, the method comprising:
    attaching a first end of a strap to an injured leg of a quadruped;
    attaching a second end of the strap to a non-injured leg of the quadruped;
    leaving the legs on the opposing side of the quadruped unencumbered to support the quadruped during the strides;
    the strap in tension during a first portion of each of the strides to force the injured leg to move with the non-injured leg; and
    the strap being slack during a second portion of each of the strides.

13. The method of claim 12, further comprising attaching the strap to the injured leg and the non-injured leg on a same side of the quadruped.

* * * * *